United States Patent [19]

Kelton

[11] Patent Number: 4,696,797
[45] Date of Patent: Sep. 29, 1987

[54] SUSPENSION LIQUID SEPARATOR

[75] Inventor: Arden A. Kelton, Fountain Valley, Calif.

[73] Assignee: Environmental Diagnostics, Inc., Irvine, Calif.

[21] Appl. No.: 723,162

[22] Filed: Apr. 15, 1985

[51] Int. Cl.$^4$ .................. G01N 1/18; B01D 15/08
[52] U.S. Cl. ............................ 422/101; 422/58; 210/321.1; 210/433.2; 210/435; 210/927; 73/863.23
[58] Field of Search .............. 422/101, 58; 210/321.1, 210/927, 433.1, 433.2, 435, 509; 73/863.23

[56] References Cited

U.S. PATENT DOCUMENTS

| | | | |
|---|---|---|---|
| 3,660,033 | 5/1972 | Schwartz | 23/230 R |
| 4,289,623 | 9/1981 | Lee | 210/433.2 X |
| 4,294,594 | 10/1981 | Sloane, Jr. et al. | 210/927 X |
| 4,318,813 | 3/1982 | Edelman et al. | 210/433.2 X |
| 4,369,112 | 1/1983 | Vincent et al. | 210/433.2 |

*Primary Examiner*—Michael S. Marcus
*Assistant Examiner*—Lynn M. Kummert
*Attorney, Agent, or Firm*—Thomas P. Mahoney

[57] ABSTRACT

A liquid suspension separator of simple, one-piece construction is provided for field tests such as bovine testing. The liquid suspension separator includes a housing having a separator chamber incorporating a filter body characterized by its ability to laterally filter the particulates of the suspension from the liquid component thereof. The housing incorporates eluant, liquid suspension and discharge ports and the liquid component of the suspension can be immediately collected to permit a test or tests to be run thereupon. One of the embodiments of the separator includes a test chamber which already incorporates a test specimen reactive to the liquid component of the suspension to permit an immediate test to be conducted in the field.

5 Claims, 11 Drawing Figures

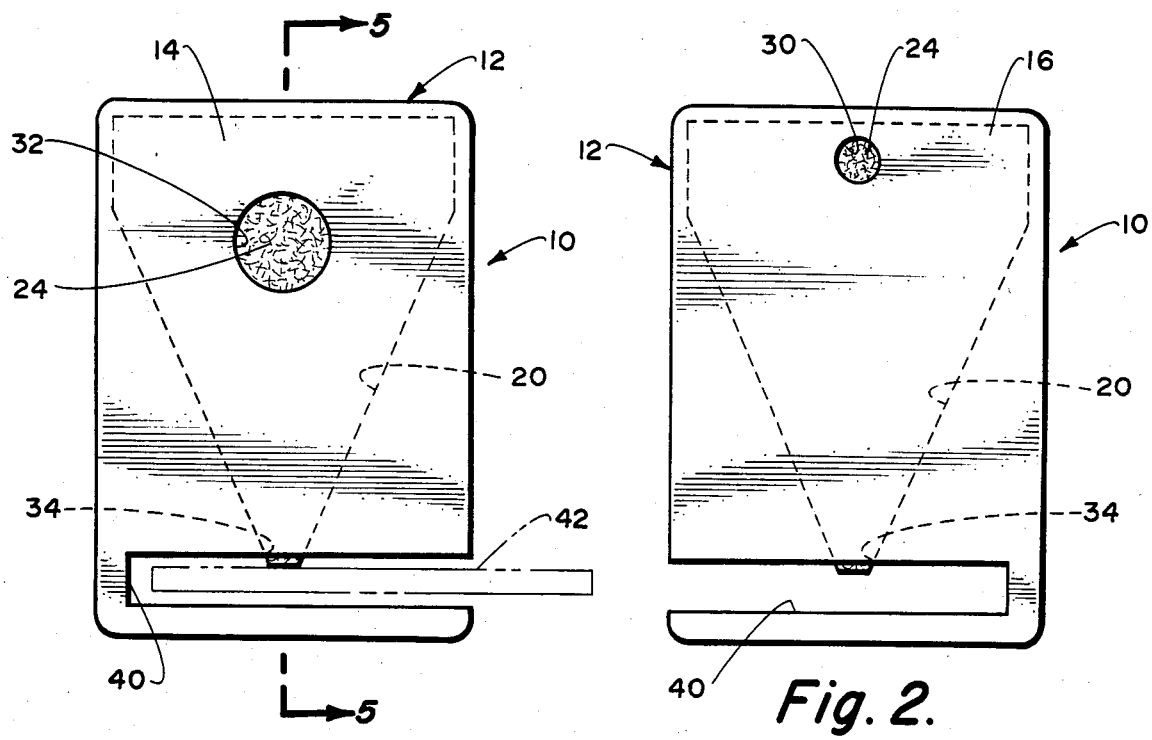
Fig. 1.
Fig. 2.
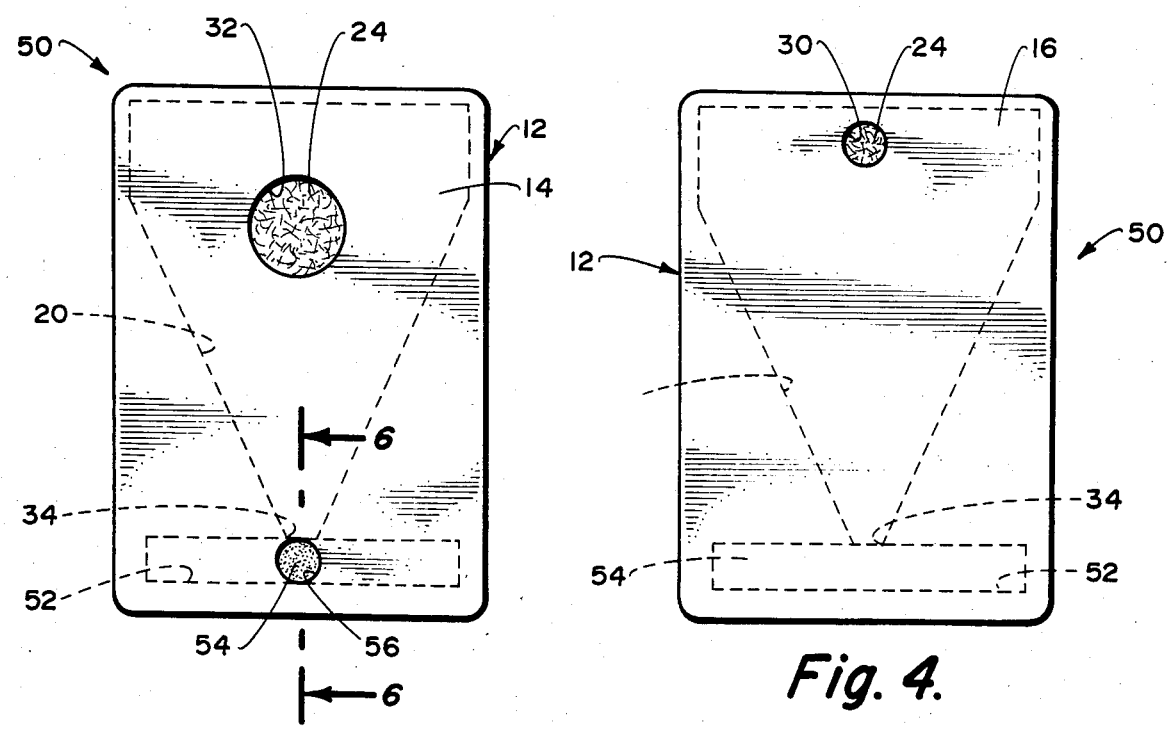
Fig. 3.
Fig. 4.

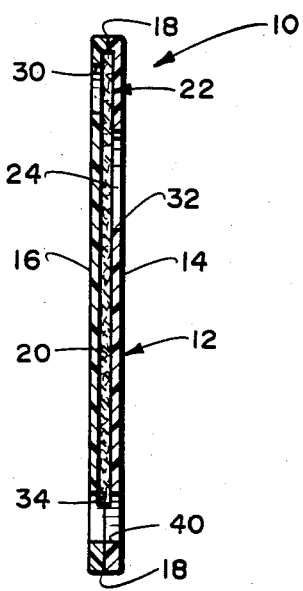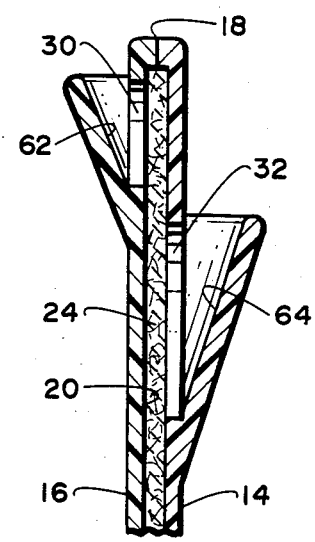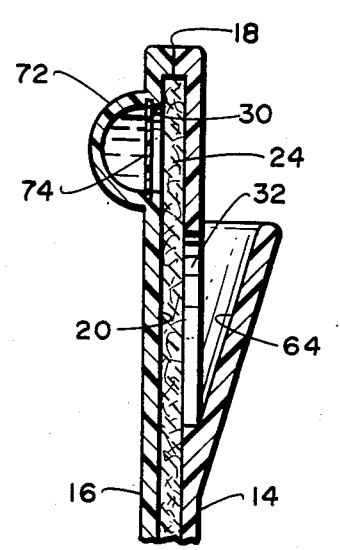
Fig. 5.  Fig. 7.  Fig. 8.
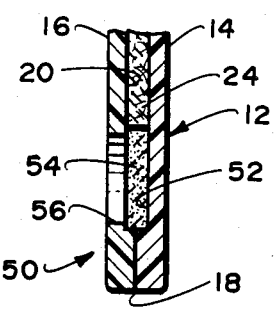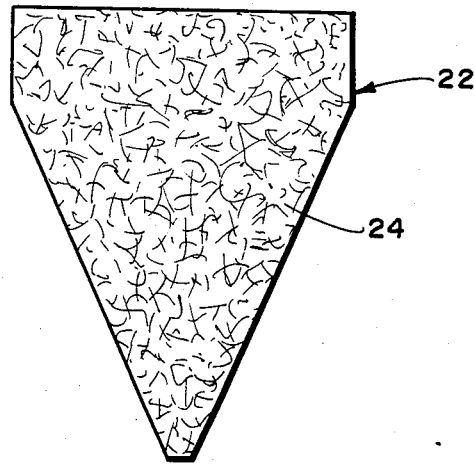
Fig. 6.  Fig. 9.
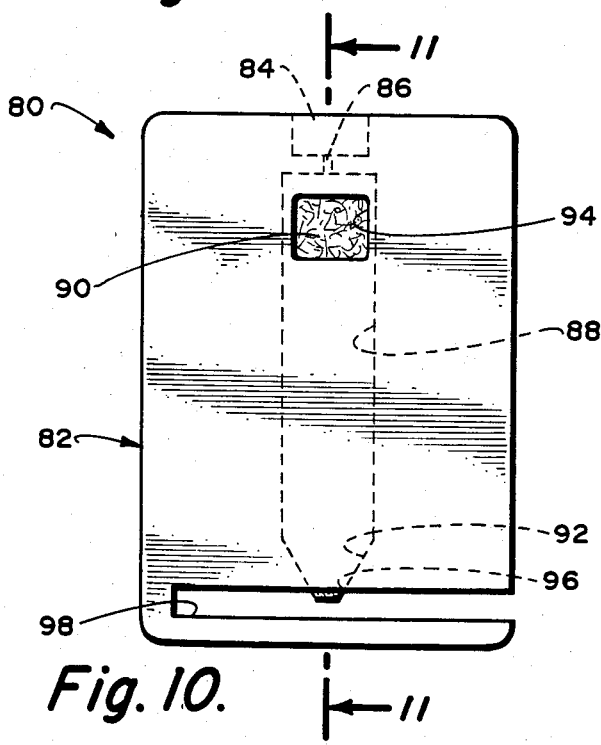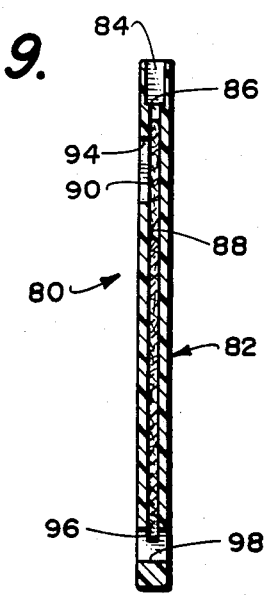
Fig. 10.  Fig. 11.

SUSPENSION LIQUID SEPARATOR

BACKGROUND OF THE INVENTION

This invention relates to liquid suspension separators and, more particularly, to a liquid suspension separator which will permit separation of the suspension liquid from the suspended particulates.

At the present time, the separation of particulates from suspensory liquid as, for example, the particulates from blood serum, entails the subjection of the blood sample to laboratory procedures which are both elaborate and expensive. Such procedures, of course, cannot be utilized in field testing where tests on the suspensory liquid are indicated.

For instance, it is well known that a large percentage of slaughtered hogs are infected with trichinosis and that many beef carcasses are infected with various types of parasites such as worms and the like. However, the testing of the carcasses to determine the presence of such infestations entails the dissection of portions of the carcasses or the obtention of blood samples from the individual carcasses and the laboratory separation and testing of the samples.

Present-day blood separation and testing procedures require that the specimens be drawn from individual carcasses, transported to a laboratory for separation and then subjected to laboratory testing. As a matter of fact, such procedures have been followed in some countries, but the expense of such testing greatly increases the ultimate cost of the meat derived from the carcasses.

OBJECTS AND ADVANTAGES OF THE INVENTION

It is, therefore, an object of my invention to provide a liquid suspension separator which can be utilized in slaughterhouses or similar environments to conduct blood separations resulting in liquid test samples which can be immediately subjected to the requisite test or assay to indicate the infestation of the carcass being subjected to the test.

It should be understood that, while the application and utilization of the liquid suspension separator is described herein in conjunction with tests on carcasses and the like to determine the infestation of the carcass by various types of parasites, the liquid suspension separator may be utilized in many applications, including emergencies which occur in connection with injuries to human beings or in veterinary applications involving the treatment of animals. In other words, it is not intended that the application of the teachings of the invention be limited solely to the ascertainment of the infestation in edible carcasses.

Another object of my invention is the provision of a separator of the aforementioned character which includes a housing incorporating a separator chamber. A number of ports are provided by the housing in communication with the separator chamber including an eluant port, a liquid suspension port and a discharge port.

The eluant port is adapted to receive eluant which is introduced into the separator chamber for a purpose which will be described in greater detail below. Of course, the liquid suspension port receives the suspension, such as blood, for suitable separation in the separator chamber.

In turn, the discharge port discharges the liquid component of the suspension after the particulates have been filtered therefrom in a manner to be described in greater detail below.

The housing may be fabricated from a wide variety of suitable materials which are impervious to liquid flow including vinyl or polyethylene plastics or the like. The housing may be formed by injection or blow molding and is usually of sufficient size to receive the required eluant dosage and liquid suspension adequate for the provision of a requisite liquid test specimen.

Incorporated in the separator chamber is a filter consisting of a body of filter material. The body may be formed from any of a number of depth-type planar filter materials capable of entrapping formed suspension elements or particulates during eluant-induced flow between the filter surfaces. Exemplary of such a material is glass microfiber filter material which is available in a range of porosities suitable for entrapping formed elements or particulates from a number of suspensions such as blood and tissue washes.

An inherent characteristic of the filter material is that the filter porosities are interconnected in the plane of the filter. A conventional filter which is capable of entrapping formed suspension elements or particulates, but which is not suitable for the practice of the invention is a planar membrane filter which has porosities connecting its opposite surfaces but offers no pathway for lateral flow generally parallel to and between the surfaces.

An additional object of the invention is the provision of a separator of the aforementioned character in which the aforesaid filter body is disposed in intimate contact with the adjacent walls of the separator chamber in order that neither eluant nor fluid suspension bypass the porosities of the filter. Such bypassing would, in the case of the eluant, provide an unduly diluted fluid test specimen and, in the case of the suspension, permit the bypassing of particulates or other suspended materials to the discharge port.

Another object of my invention is the provision of a separator of the aforementioned character having receptor means incorporated in the housing thereof whereby a test or assay device may be inserted into juxtaposition to the liquid discharge port of the separator in order that an immediate test may be accomplished.

A further object of my invention is the provision of a separator of the aforementioned character in which the test or assay specimen is incorporated in the housing of the separator immediately adjacent to and in fluid communication with the discharge port. With this embodiment of the invention an immediate test can be achieved without the utilization of an ancillary testing device.

BRIEF DESCRIPTION OF THE DRAWINGS

Other objects and advantages of the invention will be apparent from the following specification and the accompanying drawings, which are for the purpose of illustration only, in which:

FIG. 1 is a front elevational view of a separator constructed in accordance with the teachings of the invention;

FIG. 2 is a rear elevational view;

FIG. 3 is a front elevational view of an alternative embodiment of the invention;

FIG. 4 is a rear elevational view of the embodiment of FIG. 3;

FIG. 5 is a vertical sectional view taken on the broken line 5—5 of FIG. 1;

FIG. 6 is a fragmentary, enlarged vertical sectional view taken on the broken line 6—6 of FIG. 3;

FIG. 7 is an enlarged fragmentary sectional view showing an alternative construction of the eluant and suspension ports;

FIG. 8 is an enlarged fragmentary sectional view showing an alternative embodiment of the eluant reservoir of the separator;

FIG. 9 is a top plan view of a typical filter body utilized in conjunction with the separator of the invention;

FIG. 10 is a front elevational view of an alternative embodiment of the separator of the invention; and FIG. 11 is a vertical sectional view taken on the broken line 11—11 of FIG. 10.

DESCRIPTION OF PREFERRED EMBODIMENTS OF THE INVENTION

Referring to the drawings, and particularly to FIGS. 1-2, 5 and 9 thereof, I show a liquid suspension separator 10 which is incorporated in a substantially rectangular housing 12 fabricated from any suitable inert material such as vinyl or polyethylene plastics.

The housing 12, as best shown in FIG. 5 of the drawings, consists of a front section 14 and a rear section 16, said sections being joined at their abutting surfaces 18 by means of a suitable adhesive. The front and rear sections 14 and 16 of the housing are configured to provide, in conjunction, a separator chamber 20, as best shown in FIG. 5 of the drawings.

The separator chamber 20, as best shown in FIG. 5 of the drawings, incorporates a filter 22 constituted by a filter body 24, said filter body being illustrated in FIG. 9 of the drawings as being generally of triangular configuration in plan.

The shape of the separator chamber is of the same shape as the filter body 24 and the inner walls of the chamber 20 are closely juxtaposed to the edges and parallel surfaces of the filter body to prevent bypassing of eluant or the liquid suspension.

As previously mentioned, the filter body 24 is fabricated from any of a number of depth-type planar filter materials capable of entrapping formed suspension elements or particulates during flow between the parallel surfaces of the filter contained in the separator chamber 20. Illustrative of such filter materials is a glass microfiber filter which is available in a range of porosities suitable for entrapping particulates from any number of suspensions of interest including blood and tissue washes.

As previously mentioned, it is absolutely necessary that the porosities of the filter materials be interconnected in the plane of the filter to facilitate flow of the suspension and eluant from one end of the filter to the other rather than between the eluant and suspension receiving ports.

The housing 12, as best shown in FIGS. 1-2 and 5 incorporates an eluant receiving port 30 which permits a suitable eluant, such as a balanced salt solution, to be introduced into the separator chamber 20. Located in the front section 14 of the housing 12 is a suspension receiving port 32 through which the suspension, such as blood, may be introduced to the separator chamber 20.

Located in juxtaposition to the lower extremity of the filter body 24 is a liquid discharge port 34 whose dimension may be of a size requisite to the desired rate of flow of the liquid component of the suspension from the separator chamber 20.

It will be noted that the precise conformity of the mass of the filter body 24 to the shape of the separator chamber 20 is required in order that the bypassing alluded to hereinabove be avoided and the substantially triangular configuration of the filter body 24 in separator chamber 20 has been chosen to achieve such conformity. In addition, the greater width of the filter body 24 is located adjacent the eluant and liquid suspension introductory ports so that the relatively large quantity of liquid injected through these ports may be adequately received by the filter body 24 and conveyed through the gradually restricted area of the filter body 24 to the inverted apex of the generally triangular configuration of the filter body 24.

Thus, the eluant introduced through the eluant port 30 carries the introduced suspension through the gradually restricted area of the filter body 24 and the particulates are suspended in the interstices of the filter body until the liquid component of the suspension is delivered to the discharge port 34.

It is also desirable to have the lower extremity of the filter body 24 projecting through the discharge port 34 so that physical contact with the relevant portion of a test or assay device may be obtained.

By insuring physical contact between the lower extremity of the filter body 24 and the relevant portion of a test or assay device, the necessity for a substantial flow of the liquid component of the suspension is eliminated and, thus, a large amount of eluant need not be applied to the filter body 24 through the eluant port 30.

The slot 40 may be provided in the lower extremity of the housing 12 to act as a guide for the introduction of a test or assay device 42, as best shown in FIG. 1 of the drawings. The relevant portion of the device 42 can be introduced into the slot 40 and the filtered liquid component of the suspension be contacted thereby to provide an immediate indication of the desired chracteristic of the liquid component of the suspension being sought.

Although I have disclosed the utilization of a glass microfiber filter and its incorporation in the separator chamber 20, there are other means available for restricting the flow of eluant and the liquid portion of the suspension to the body of the filter. For instance, the filter body 24 can be sandwiched between sheets of nonporous material parallel to and in contact with the filter surfaces and edges. A typical material for such enclosing sheets is sheets of vinyl plastic which can be heat-sealed at the edges.

The enclosing sheets may be pierced to provide access to the eluant, suspension and discharge ports. It was also conceivable that a filter utilizing the sheets as the housing instead of the relatively rigid housing formed from polyethylene might be utilized with the ports provided in the sheets in the same manner as in the more rigid housing.

An alternative embodiment of the invention is disclosed at 50 in FIGS. 3, 4 and 6 of the drawings wherein the same reference numerals as were utilized in discussing identical components of the previously discussed embodiment are utilized.

The essential difference between the previously discussed embodiment 10 and the present embodiment 50 lies in the provision of a test chamber 52 in the lower extremity of the housing 12 in immediate juxtaposition to and in fluid communication with the discharge port 34. Located in the test chamber 52 will be an assay or test composite 54 suitable for the test being conducted. Therefore, the eluted liquid portion of the suspension is transferred to the assay or test chamber for immediate analysis. A viewing port 56 may be provided in the wall of the test chamber 52 to permit visual apperception of the test results.

Although I have disclosed, in the previous embodiments 10 and 50 of the invention simple injection ports for the eluant and suspensions, it is conceivable that troughlike reservoirs 62 and 64 be provided adjacent the eluant and suspension ports 30 and 32, respectively, see FIG. 7, so that the required dosage can be placed in the troughlike reservoirs or receptacles 62 and 64 to permit the absorption of the eluant and suspension into the fibrous interstices of the filter body 24.

Alternatively, as best illustrated in FIG. 8 of the drawings, a sealed capsule 72 can be provided adjacent the eluant port 30 containing the requisite amount of eluant previously determined to be necessary to convey the liquid component of the suspension to the discharge port 34. The sealed capsule 72 incorporates a rupturable area 74 which, when the capsule 72 is compressed between the fingers, will be ruptured to permit the flow of eluant into the separator chamber 20.

The separator of the invention may be utilized to separate a quantity of the liquid component of the suspension by dosing the filter body 24 through the suspension port 32. The suspension enters the porosities of the filter body 24 which permit liquid flow but entrap the formed suspension elements or particulates.

A predetermined volume of eluant fed from the reservoir through the eluant port 30 displaces the liquid portion of the suspension from the suspension port 32 toward the discharge port 34 in a path determined by the triangular configuration of the filter body 24 and separator chamber 20. The volume of eluant is selected so that the liquid portion of the suspension will be displaced through the discharge port 34, while the eluant is retained within the filter body 24.

A specific and particular example of the use of the separator of the invention is the obtaining of an aliquot of the liquid portion of bovine blood for the determination of parasitic infections in beef carcasses. The separator is utilized in the slaughterhouse to obtain the blood sample and is attached to the beef carcass during processing.

In usage, the blood sample is added at the suspension port 32 and the formed blood elements or particulates are trapped within the filter body 24 as the eluant displaces the liquid portion of the blood longitudinally and laterally through the body of the filter to the discharge port 34 where it is transferred to the test or assay strip or to such other object as may be desired.

Another embodiment 80 of the separator of the invention is shown in FIGS. 10 and 11 of the drawings. The separator 80 includes a generally rectangular housing 82 which may be fabricated from the same types of plastic as the previously discussed embodiments and which includes an eluant reservoir 84 having an eluant port 86 at the bottom thereof communicating with a separator chamber 88 which is formed in the housing 82.

Located in the separator chamber 88 is a filter body 90 which is of generally elongated rectangular configuration, but which has a lower truncated conical portion 92, as best shown in FIG. 10 of the drawings.

Formed in the wall of the housing in overlying relationship with the filter body 90 and below the eluant port 86 is a suspension liquid port 94 which is large enough to permit a sample of the suspension liquid to be placed upon the filter body 90 and which is located below the eluant port 86 to permit the flow of eluant from the eluant reservoir 84 to cause the movement of the liquid component of the suspension liquid downwardly by gravity toward the discharge port 96.

As previously mentioned, the extreme lower end of the filter body 90 may protrude through the discharge port 96 into a receptor slot 98 in the housing 82 to permit a test assay to be inserted into contiguity to the lower extremity of the filter body 90 and the discharge port 96.

Of course, as previously mentioned, the fabrication of the housing of the various embodiments can be accomplished in a wide variety of ways by the utilization of an equally wide variety of manufacturing expedients. For instance, the separator 80 may be fabricated from an injection molded blank in which the separator chamber is constituted by an elongated slot for the reception of the filter body which slot is later covered by a liquid-proof cover, such as a liquid-proof label or the like.

Therefore, the expensive, time-consuming and impractical laboratory testing of beef blood samples is eliminated and it becomes economically feasible by the utilization of the separator manufactured in accordance with the teachings of this invention to test individual beef carcasses as they are transported along the line in the slaughterhouse.

It will be apparent to those skilled in the art that various embodiments other than those disclosed hereinabove can be constructed which will fall within the scope of the appended claims, although differing in details of construction.

I claim:

1. In a suspension liquid separator, the combination of: a housing having a separator chamber and an eluant port, a liquid suspension receiving port and a liquid discharge port communicating with said chamber; and a depth-type, planar, liquid filter body located in said chamber in juxtaposition to said ports, said filter body having one portion adjacent said eluant and liquid suspension receiving ports and another portion adjacent said liquid discharge port, the width of said chamber at said another portion being configured such that said another portion completely fills said chamber, whereby fluid flow is restricted within said filter body.

2. The separator of claim 1 in which said filter body is flat and incorporates co-planar surfaces juxtaposed to walls of said chamber to prevent bypassing of liquid suspension and eluant around said filter body.

3. The separator of claim 2 in which said chamber and said filter body are of generally flat, triangular configuration having a base and an apex with the base of said triangular filter body juxtaposed to said liquid suspension receiving and eluant ports and the apex of said body juxtaposed to said discharge port, said filter body corresponding to said triangular configuration of said chamber to cause liquid flow from said eluant and liquid suspension ports to said discharge port.

4. In a liquid suspension separator for providing a liquid test specimen from which particulates have been removed, the combination of: a housing incorporating a separator chamber, said housing having eluant and liquid suspension ports located at one extremity of said chamber and a discharge port communicating with another extremity of said chamber; a depth-type planar liquid filter body located in said separator chamber in juxtaposition to said ports, said filter body having one portion adjacent said eluant and liquid suspension receiving ports and another portion adjacent said liquid discharge port, the width of said chamber at said another portion being configured such that said another portion completely fills said chamber, whereby fluid flow is restricted within said filter body said filter body incorporating laterally operative filtration passages whereby eluant and liquid suspension introduced into said chamber through said respective ports will be conveyed to said discharge port while said particulates are retained in said filter body; and receptor means on said another extremity adjacent said discharge port for receiving, positioning and holding a test device in immediate proximity to said discharge port.

5. The separator of claim 4 in which said receptor means comprises a receptor slot formed in said body immediately adjacent said discharge port and adapted to receive said test device.

* * * * *